United States Patent
Herrera et al.

(10) Patent No.: US 7,361,800 B2
(45) Date of Patent: Apr. 22, 2008

(54) PROCESS FOR THE SEPARATION OF OLEFINS FROM PARAFFINS USING MEMBRANES

(75) Inventors: Patricio S. Herrera, Calgary (CA); Xianshe Feng, Waterloo (CA); John Donald Payzant, Edmonton (CA); Jeong-Hoon Kim, Taejon (KR)

(73) Assignee: Monteco Ltd. (CA)

( * ) Notice: Subject to any disclaimer, the term of this patent is extended or adjusted under 35 U.S.C. 154(b) by 581 days.

(21) Appl. No.: 10/818,557

(22) Filed: Apr. 5, 2004

(65) Prior Publication Data

US 2004/0215045 A1 Oct. 28, 2004

(30) Foreign Application Priority Data

Apr. 25, 2003 (CA) .................................. 2426629

(51) Int. Cl.
- C07C 7/00 (2006.01)
- C07C 7/144 (2006.01)
- B01D 53/22 (2006.01)

(52) U.S. Cl. ............... 585/818; 585/809; 585/843; 585/844; 585/845; 585/848; 95/45; 95/50

(58) Field of Classification Search ............... 585/809, 585/818, 843–845, 848; 95/45, 50
See application file for complete search history.

(56) References Cited

U.S. PATENT DOCUMENTS

| | | | |
|---|---|---|---|
| 4,623,704 A | 11/1986 | Dembicki et al. | |
| 4,808,313 A | 2/1989 | Michizuki et al. | |
| 4,944,881 A | 7/1990 | Michizuki et al. | |
| 4,985,147 A | 1/1991 | Mochizuki et al. | |
| 5,034,134 A | 7/1991 | George et al. | |
| 5,352,272 A | 10/1994 | Moll et al. | |
| 5,670,051 A | 9/1997 | Pinnau et al. | |
| 5,679,133 A | 10/1997 | Moll et al. | |
| 5,837,032 A | 11/1998 | Moll et al. | |
| 6,271,319 B1 | 8/2001 | Baker et al. | |
| 6,339,182 B1 * | 1/2002 | Munson et al. | 585/809 |
| 6,414,202 B1 | 7/2002 | Baker et al. | |
| 6,525,236 B1 | 2/2003 | Baker et al. | |

* cited by examiner

Primary Examiner—Glenn Caldarola
Assistant Examiner—In Suk Bullock
(74) Attorney, Agent, or Firm—Katten Muchin Rosenman LLP

(57) ABSTRACT

Chitosan membranes chelated with silver or cuprous material may be used to separate olefins from a mixture of olefins and paraffins. The feed stream is humidified, demisted, treated to remove sulfur compounds and passed to a cell having a chitosan membrane containing chelated silver or cuprous compounds. The process has a reasonable flux rate and is operable at reasonable temperatures and pressures. The process could be used in an olefin separation train.

20 Claims, 3 Drawing Sheets

PROCESS FOR THE SEPARATION OF OLEFINS FROM PARAFFINS USING MEMBRANES

FIELD OF THE INVENTION

The present invention relates to the separation of paraffins from olefins. More particularly the present invention relates to the separation of paraffins from olefins using semi-permeable membranes desirably polysaccharide membranes particularly chitosan membranes. In one embodiment of the present invention alpha olefins, and particularly ethylene or propylene or mixtures there of may be separated from paraffins.

BACKGROUND OF THE INVENTION

U.S. Pat. Nos. 4,808,313; 4,944,881; and 4,985,147 to Mochizuki et al., issued Feb. 28, 1989; Jul. 31, 1990; and Jan. 15, 1991, respectively, all assigned to the Japanese Agency of Industrial Science and Technology teach the formation of a chitosan semi-permeable membrane and its use in separating water from various organic compounds. The reference does not teach or suggest that polysaccharide membranes could be useful in a process to separate olefins from paraffins, nor does the patent teach the process steps for the separation of olefins from paraffins using such a membrane.

U.S. Pat. No. 4,623,704 issued Nov. 18, 1986 to Dembicki et al., assigned to the Dow Chemical Company teaches passing a stream of gaseous ethane and ethylene from a solution polymerization through a semi permeable hollow fiber to remove ethylene from the feed and increase the concentration of ethylene in the permeate (i.e. alkene/alkane separation). The permeate is then recycled back to the polymerization reactor. The reference teaches a number of semi-permeable membranes and particularly cellulose esters such as the acetate, diacetate, and triacetate. The reference fails to teach the specific steps of the present invention including the removal of sulfur compounds, humidification of the feed stream with water, and the use of a demistifier to remove droplets from the feed stream. Additionally, the reference totally fails to teach chelating a silver or copper (I) (e.g. cuprous) metal compound in the semi-permeable membrane.

U.S. Pat. No. 5,034,134 issued Jul. 23, 1991 to George et al., assigned to Union Carbide Chemicals and Plastics Technology Corporation discloses the use of semi-permeable membranes to separate impurities and/or additives from a liquid stream comprising ethylene glycol and water. The patent does not teach separating alkenes from alkanes (paraffins) in a gas phase (e.g. pervaporation).

There are a number of patents in the name of Moll, assigned to the Dow Chemical Company that teach the separation of gases at low temperatures. Representative of this art are U.S. Pat. Nos. 5,352,272; 5,679,133; and 5,837,032. These patents teach the use of glassy polymers or rubbery polymers as the semi-permeable membrane. The references fail to teach the use of polysaccharides and in particular chitosan as the semi-permeable membrane.

There are a number of patents assigned to Membrane Technology and Research, Inc. including U.S. Pat. Nos. 6,271,319; 6,414,202; and 6,525,236. These patents also teach the separation of gases using rubbery or glassy polymers. U.S. Pat. No. 6,271,319 is of interest as it refers to the incorporation of silver ions to improve the transfer of propylene across the membrane.

U.S. Pat. No. 5,670,051 issued Sep. 27, 1997 to Pinnau et al., assigned to Membrane Technology and Research, Inc. discloses separating olefins from a stream containing other components using a membrane which is made from a polymer selected from the group consisting of rubbery polymers (e.g. silicon rubber), a polyalkyl oxide (e.g. poly (ethylene oxide)), polymers containing ether linkages (e.g. epihalohydrin or propylene oxide/allylglycidalether copolymer), polyetherpolyamide block copolymers and polyesters such as polyalkyl adipates, succinates sebacates and so on. The patent does not disclose or suggest the polysaccharide semi-permeable membranes of the present invention. Further the patent teaches the membrane is preferably used in a dry mode. The patent teaches that silver nitrate is not suitable as a material to incorporate into the membrane.

The present invention seeks to provide a relatively simple process to separate olefins, preferably $C_{2-8}$ olefins, desirably alpha olefins, from $C_{1-10}$ preferably $C_{1-8}$ paraffins. The process is energy efficient and uses a polysaccharide membrane as the semi-permeable membrane preferably on a support membrane.

SUMMARY OF THE INVENTION

The present invention provides a process to treat a gaseous feed stream comprising at least from 99 to 1 mole % of one or more $C_{2-8}$ olefins and 1 to 99 mole % of one or more $C_{1-8}$ paraffins said stream comprising less than 500 ppm of $C_{2-4}$ acetylenes which comprises:

(i) passing said stream through an adsorption bed to reduce the concentration of sulfur compounds in the stream to less than 100 ppm;

(ii) passing the resulting stream through a humidifier so that the stream takes up at least 85% of the water required to saturate the stream;

(iii) passing the resulting stream through a demister to remove any liquid droplets entrained in the stream;

(iv) passing the resulting stream at a pressure from 14 to 1500 psig, and a temperature from 20° C. to 60° C. to the feed side of a composite membrane comprising a support layer permeable or semi-permeable to said olefin and a polysaccharide layer in which has been chelated from 30 to 60 weight % on a dry basis based on the weight of the polysaccharide layer of one or more compounds selected from the group consisting of copper and silver compounds capable of forming complexes with at least one olefin in said stream or a mixture thereof, so that not less than 80 mole % of the olefins in said feed stream pass through said composite membrane;

(v) recovering a permeate stream comprising not less than 90 mol % of olefin and not more than 10 mole % of paraffin.

DETAILED DESCRIPTION

Figure 1:
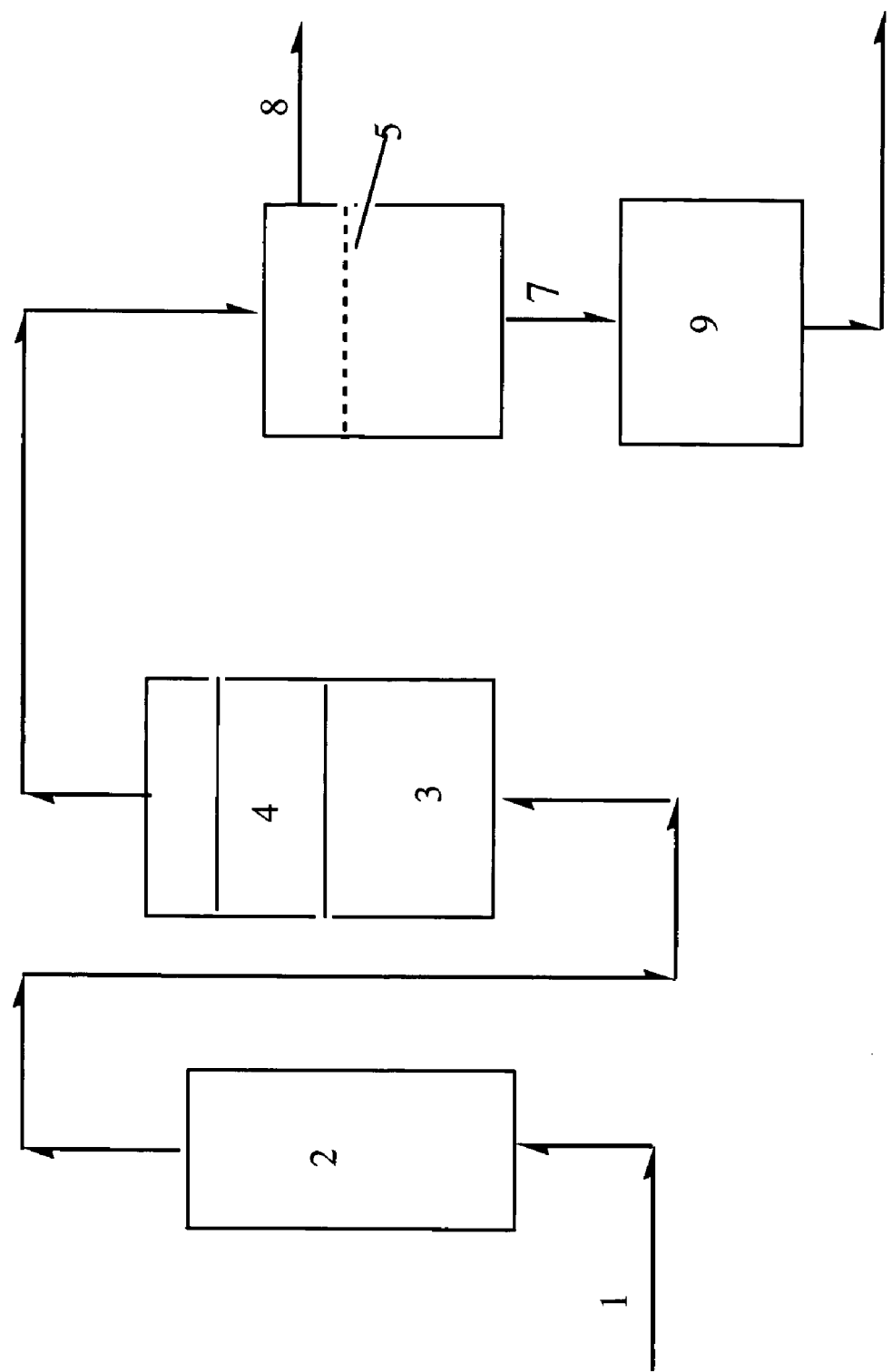
FIG. 1 shows a schematic drawing of the process of the present invention.

The process of the invention will be described in accordance with FIG. 1. The feed stream 1 comprising a mixture of olefins and paraffins (alkanes) passes through a guard bed 2 to remove sulfur-containing compounds. The feed stream should have an acetylenes content of less than 500 ppm. The methods of removing or converting acetylenes to alkylenes in a hydrocarbon feed stream are well known to those skilled in the art. The resulting stream then passes through a humidifier 3 to humidify the stream. The stream then passes through a demister 4, to remove water droplets which may be entrained in the stream. The humidified stream is then fed to a semi-permeable membrane 5. The olefins preferentially pass through the semi-permeable membrane giving a permeate stream 7 and a retentate stream 8. The permeate stream is richer in olefins and the retentate stream is richer in paraffins. The permeate stream may be passed through a dryer 9 to remove water. The retentate stream may be recycled back to the process.

In accordance with the present invention a feed stream comprising a mixture of olefins and paraffins is passed through a guard bed. The feed stream may comprise from 99 to 1 mole % of one or more $C_{2-8}$ alpha olefins and from 1 to 99 mole % of one or more $C_{1-10}$ paraffins. Typically, the feed stream comprises at least 60 mole % of one or more $C_{2-8}$ alpha olefins and up to 40 mole % of one or more $C_{1-10}$, preferably $C_{1-8}$, paraffins. Generally the feed stream may comprise 70 to 90 mole % of olefins and from 30 to 10 mole % of paraffins. The feed stream has already been treated to reduce the level of acetylenes, preferably $C_{2-4}$ acetylenes particularly acetylene per se, to less than 500, preferably less than 100, most preferably less than 50, desirably less than 25, most desirably less than 15 parts per million by weight (ppm).

The feed stream is passed through a guard bed to reduce the concentration of compounds containing sulfur to less than 100, preferably less than 30, most preferably less than 10 ppm. Suitable guard beds are known to those skilled in the art. Typically the guard bed or beds are adsorption beds generally containing a molecular sieve adsorbent, preferably a zeolite type adsorbent, particularly Zeolite A. Some zeolites will adsorb water from a gas passing over or through them. However, as the resulting treated feed stream is subjected to a humidification step this should not be a significant issue.

The treated feed stream is then passed through a humidifier. The humidifier operates at a temperature from 0° C. to 95° C., typically from 20° C. to 50° C. In the humidifier the stream passes through a water bath and should take up at least 85%, preferably greater than 95%, most preferably 100% of the water required to saturate the stream.

The humidified stream then passes through a demister to remove water droplets which may have become entrained in the stream.

The resulting stream then passes to a semi-permeable membrane. The membrane is typically supported. The support may be made from one or more members selected from the group consisting of polyesters, polyamides, polyimides, polyacrylonitrile, polysulphones and polycarbonates. Physically the support may be a film (e.g. a cast film) or it may be in form of a non-woven web (e.g. fibers) or hollow fibers. The support layer may have a thickness from 30 to 200 microns preferably from 50 to 150 microns. Methods for casting such polymers or spinning the polymers into fiber and subsequent conversion into a non-woven web or converting the polymers into hollow fibers are well known to those skilled in the art.

The semi-permeable membrane is a polysaccharide membrane in which has been chelated from 30 to 60, preferably from 45 to 55 weight % on a dry basis on the weight of said polysaccharide of a silver or copper (I) compound. Care should be taken if using a mixture of silver and copper (i) compounds as a redox reaction may occur which may damage the semi-permeable membrane.

Examples of polysaccharide membrane of the present invention include natural polysaccharides such as alginic acid, pectic acid, chondroitin, hyaluronic acid and xanthan gum; cellulose, chitin, pullulan, derivatives such as $C_{1-6}$, preferably $C_{1-4}$, esters, ether and alkylcarboxy derivatives thereof and phosphates of these natural polysaccharide such as partially methylesterified alginic acid, carbomethoxylated alginic acid, phosphorylated alginic acid and aminated alginic acid; salts of anionic cellulose derivatives such as carboxymethyl cellulose, cellulose sulfate, cellulose phosphate, sulfoethyl cellulose and phosphonoethyl cellulose; and semi-synthetic polysaccharides such as guar gum phosphate and chitin phosphate. Specific examples of membranes of polysaccharides include those composed of salts of chitosan and its derivatives such as N-acylated chitosan, chitosan phosphate and carbomethoxylated chitosan. Of these, membranes composed of alginic acid, and salts and derivatives thereof, chitosan and salts and derivatives thereof cellulose and derivatives thereof (other than the mono-, di-, and tri-acetate derivatives thereof which are not intended to be included in the present invention) are preferred in view of their film-formability, mechanical strength and film functions. The gas separation membrane of this invention also include membranes composed of blends of a major amount (e.g. at lest 60 weight %) of the polysaccharides and lesser amounts (e.g. up to 40 weight %) other compatible polymeric substances, such as for example polyvinyl alcohol (PVA) or neutral polysaccharides such as starch and pullulan, and membranes composed of grafted ionized polysaccharides obtained by grafting a hydrophilic vinyl monomer such as acrylic acid.

The polysaccharide may be formed into a film by forming a solution of the polysaccharide in a dilute (less than 5%, preferably less than 2% by weight in water) acid. Preferably the acid is an organic acid such as a $C_{1-4}$ organic acid preferably acetic acid. The resulting solution may be cast as a film on a substrate such as glass or Teflon or the like (e.g. a smooth substrate to which the polymer film will have a low adhesion). The solution is then dried to form a film. In another alternative the polysaccharide is cast directly onto the support layer which may itself be a film or a non-woven support. In yet another alternative the polysaccharide is coated onto a hollow fiber substrate.

Typically, the semi-permeable membrane will have a thickness from 0.5 to 20, preferably 3 to 10 most preferably from about 5 to 8 microns and the support layer has a thickness from 30 to 200, preferably from 50 to 150, most preferably from 80 to 110 microns.

Preferably the membrane is chitosan. The chitosan (or other polysaccharide) may be deacylated by treatment with hot alkali. The polysaccharide may then be treated with a base to generate the protonated derivative ($NH_3^+$) or the unprotonated amino form ($NH_2$).

Chitosan is a generic term for deacetylation products of chitin obtained by treatment with concentrated alkalis. It is obtained by heating chitin, the principal constituent of shells of crustaceans such as lobsters and crabs to a temperature of at least 60° C. together with an alkaline solution having an alkali concentration of 30 to 50% by weight (such as an aqueous solution of sodium hydroxide) and thereby deacetylating chitin. Chemically, it is a polysaccharide having a .β-(1→4) linkage composed of D-glucosamine as basic units. Chitosan easily dissolves in a dilute aqueous solution of an acid such as acetic acid and hydrochloric acid with the formation of a salt, but when contacted again with an aqueous alkaline solution, is again coagulated and precipitated. A chitosan membrane can thus be obtained by dissolving chitosan in the aforesaid solvent (dilute aqueous acid solution), casting the solution onto a flat plate and then contacting it with an aqueous alkaline solution, or air-drying the cast membrane and contacting the dried membrane with an aqueous alkaline solution. Preferably, chitosan generally has a deacetylation degree of at least 50%, preferably at least 75%. To ionize the chitosan-type polysaccharide membrane, the amino groups of the chitosan-type polysaccharide membrane are at least partly neutralized with an acid thereby to form an ammonium salt. Examples of the acid that can be utilized for neutralization include inorganic acids such as hydrochloric acid, hydrobromic acid, sulfuric acid and phosphoric acid; and organic acids such as acetic acid, methanesulfonic acid, formic acid, propionic acid, oxalic acid, malonic acid, succinic acid, fumaric acid, maleic acid, glutaric acid, phthalic acid, isophthalic acid, terephthaic acid, trimesic acid, trimellitic acid, citric acid, aconitic acid, sulfobenzoic acid, pyromellitic acid and ethylenediaminetetraacetic acid. These acids may be used singly or in combination.

Ionization of the chitosan-type polysaccharide membrane using these acids can be effected, for example, by a method which comprises immersing the chitosan-type polysaccharide membrane in a solution containing the acid to ionize the amino groups in the membrane; or by a method which comprises subjecting the chitosan-type polysaccharide membrane to pervaporation with a mixed liquid containing the acid to convert the amino groups in the chitosan-type polysaccharide membrane successively to ammonium ions.

The chitosan-type polysaccharide membrane reacts with the silver or copper (I) compound to form a metal complex (chelate). Specifically, the monovalent metal ion is coordinated with the amino groups of the chitosan-type polysaccharide. Examples of the metal ions include copper and silver. These metal ions may be used singly.

Counter anions for the chitosan-type polysaccharide in which the metal ions are coordinated may include, for example, anions generated from inorganic acids such as sulfuric acid, nitric acid, phosphoric acid and hydrohalic acids, and anions generated from organic acids such as acetic acid.

The monovalent metal ions can be coordinated with the chitosan-type polysaccharide membrane by, for example, a method comprising subjecting the chitosan-type polysaccharide to a pervaporation treatment with a water-organic liquid mixture containing the metal salt whereby the metal ions are successively coordinated with the glucosamine rings of chitosan, or by a method comprising immersing the chitosan-type polysaccharide membrane in a solution containing the metal salt to coordinate the polyvalent metal ions. The latter method is preferred because the chitosan-type polysaccharide membrane so obtained can be immediately used for olefin/paraffin separation upon setting it in an olefin paraffin membrane separation apparatus.

The membrane has chelated therein one or more copper or silver compounds. The compounds may be selected from the group consisting of $AgNO_3$, $AgBF_4$, and cuprous compounds. Typically the film is treated with a solution of the compound to be chelated into the film. Then the film is dried, or at least partially dried, typically at a water content of not more than 75%, preferably less than 50%, most preferably from about 15 to 30% (by weight based on the dry weight of the membrane).

The membrane may take any convenient configuration. The semi-permeable membrane could be in the form of a flat sheet or a plate, sometimes referred to frame and plate construction. The semi-permeable membrane could be in the form of a spirally wound coil. The semi-permeable membrane could be in the form of a hollow fiber or a bundle of hollow fibers. The hollow fibers may have an inside diameter in the range from about 70 to about 130 microns and a wall thickness in the range from about 75 to about 110 microns. The feed mixture to be separated may flow inside or outside the hollow fibers and the feed flow may be in a direction countercurrent or concurrent with the permeate flow. The semi-permeable membrane may be modular requiring several modules.

The pressure of the feed stream to the semi-permeable membrane may be from 14 to 1,500 psig, preferably from 14 to 800 psig (96.5 KPag to 1,034 KPag preferably 96.5 KPag to 5,512 KPag). The temperature of the semi-permeable membrane may be from 20° C. to 60° C., preferably from 45° C. to 60° C.

The transmission rate of olefin across the semi-permeable membrane should be not less than 50 $sl/m^2/hr$ (standard liters per square meter per hour), preferably greater than 150 $sl/m^2/hr$, typically in the range of 160 to 200 $sl/m^2/hr$.

The selectivity of the semi-permeable membrane should be such that under the conditions of use not less than 80 mole % of the olefins in the feed stream pass through the semi-permeable membrane. The permeate should comprise not less than 90 mole % of the olefins, preferably not less than 95 mole % of olefin and more than 5 mole % of paraffin, most preferably not less than 98 mole % of olefin and not more than 2 mole % of paraffin. The permeate side of the semi-permeable membrane may be swept. When sweeping is used the permeate will be a mixture of olefin(s) and the sweeping gas which may need to be separated from the olefin(s). This may present technical difficulties if the sweep gas is an inert gas such as nitrogen or argon. However low temperature steam may be used as a sweep gas as it will keep the membrane humid and can be easily removed from the permeate stream (e.g. by condensation) to recover relatively pure olefin(s).

The permeate stream may then be dried in a drier and further processed to meet conventional commercial standards for the permeate (e.g. polymerization grade olefin). The retenate may be further processed or recycled back to the beginning of the process.

The process of the present invention may be particularly useful in the separation train of an ethylene cracker. The retentate could then be recycled back to the cracker.

The present invention will now be illustrated by the following examples wherein parts means parts by weight (e.g. grams) and % means weight % unless otherwise specified.

EXAMPLE 1

Preparation of Chitosan Membrane

A solution of chitosan was prepared by dissolving crude chitosan (Aldrich Chemical Company) in 2% Acetic Acid in water followed by filtration of the solution through a 0.45-micron filter. The resulting filtered solution contained about 1.1 wt % chitosan. A layer of this solution was cast on a glass plate and a gentle current of air was passed over it until it was substantially dry. The quantity of 1.1 wt % chitosan solution taken was calculated to give a dry chitosan membrane of about 45-micron thickness. The resulting membrane was removed from the glass surface using a knife and then placed in 0.8M NaOH in ethanol: water (5:1) to convert the ammonium groups to the free amino form. The chitosan membrane was then removed from the ethanol-water solution and washed repeatedly in water to remove ethanol and salts and finally stored in water.

EXAMPLE 2

Impregnation of the Chitosan Membrane with $AgNO_3$

Solid $AgNO_3$ was dissolved in water to afford individual aqueous solutions with concentrations of 3M $AgNO_3$, 6M $AgNO_3$, 7.5M $AgNO_3$ and 9M $AgNO_3$. Pieces of the chitosan membrane, prepared as described in Example 1, were immersed overnight (16 hours) in the appropriate concentration $AgNO_3$ solutions. The resulting membranes were assembled in the test apparatus.

EXAMPLE 3

Evaluation of $AgNO_3$ Containing Chitosan Membrane

Figure 2:
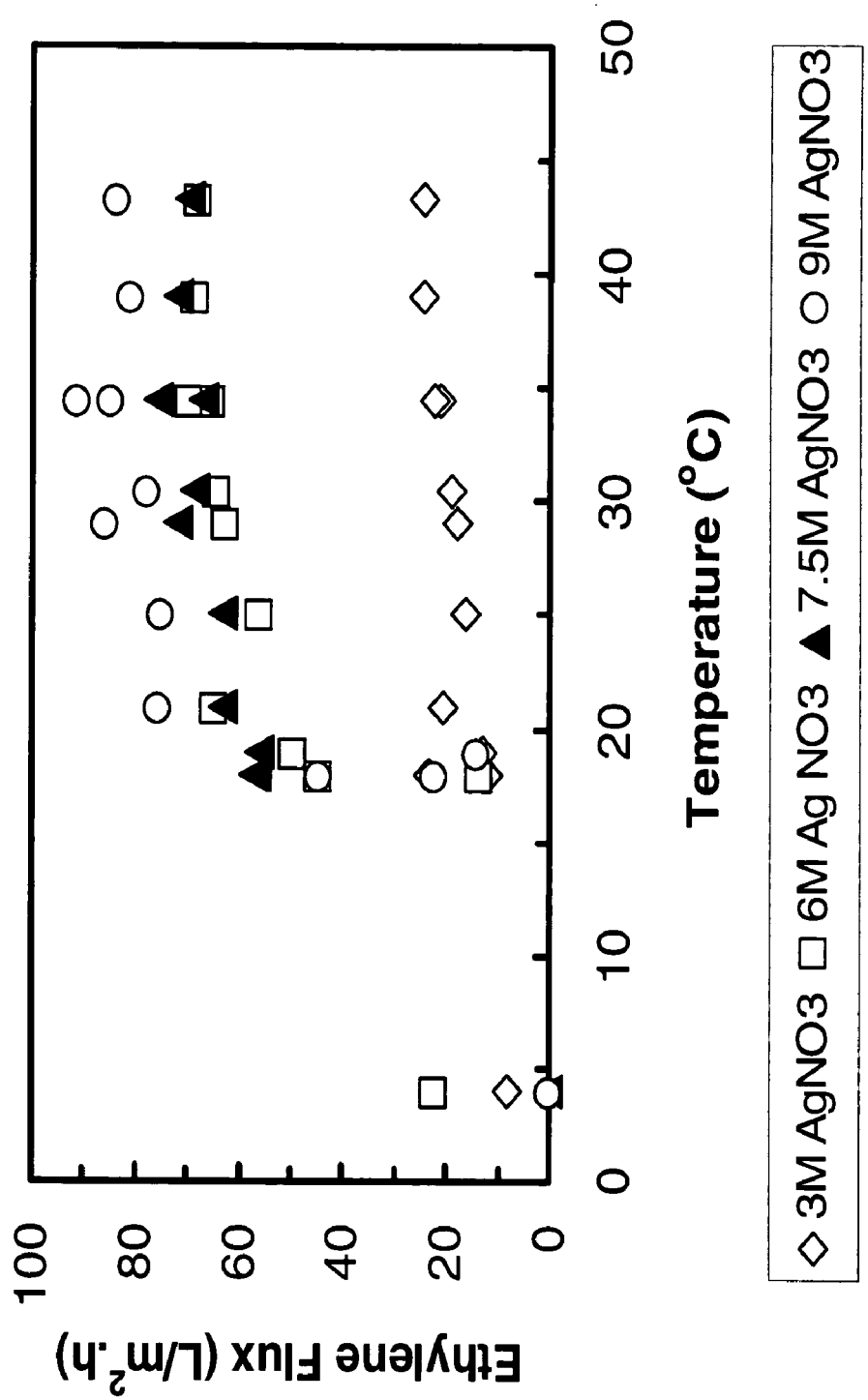
FIG. 2 is a plot of the flux rate for ethylene through chitosan membranes containing various amounts of Ag at different temperatures as determined in Example 3.

An $AgNO_3$ containing chitosan membrane, prepared as described above, was placed in a test cell. The thicknesses of the membranes were ~45 µm. The active area of the test cell was 4 cm in diameter. A test-gas mixture of ethylene (62%) and ethane (38%) was bubbled through water to humidify the test-gas and then flowed over the membrane at a rate of about 40 ml (STP) min$^{-1}$. The pressure on the test gas side of the membrane was approximately 50 psig and the pressure was approximately atmospheric on the transmitted gas side. The test cell and humidification apparatus were immersed in a water bath maintained at a controlled temperature. The gas transmitted by the membrane was analyzed using a gas chromatograph. In all cases, the purity of the transmitted gas was >99.5% ethylene. The flow of gas through the membrane was recorded as a function of temperature for chitosan membranes prepared from $AgNO_3$ containing solutions of different concentration. The data is shown in the FIG. 2.

EXAMPLE 4

Composite Membrane

The concentration of the chitosan of the aqueous acetic acid solution described in Example 1 above was increased from the 1 wt % range to about 4 wt % range by evaporation of solvent using a rotary evaporator. An approximately 100 micron layer of the 4 wt % chitosan was deposited on a micro-porous (~0.23 micron) PVDF (polyvinylidene fluoride) membrane manufactured by Millipore Co. using a metering rod manufactured by Gardco Co. The resulting chitosan layer was dried in a gentle flow of air. The resulting composite membrane was placed in 0.8 M NaOH in ethanol: water (5:1) to convert the ammonium groups to the free amino form. The composite membrane was then removed from the ethanol-water solution and washed repeatedly in water to remove ethanol and salts. The composite membrane was then immersed in a 6M $AgNO_3$ solution overnight and then mounted in the test cell in the apparatus described in Example 3 above. Gas flux through the membrane for a test-gas mixture of ethylene (62%) and ethane (38%) was about 120 litre m$^{-2}$ hr$^{-1}$ at 50 psig of test-gas at 35° C. Transmitted ethylene purity was >99.5%.

EXAMPLE 5

Propylene/Propane Permselectivity of Dense Membranes

This example illustrates the propylene/propane permselectivity of dense membranes versus membrane composition.

Chitosan membranes were prepared in same procedure as described in Example 1, except that the chitosan material was supplied by Koyowa Technos Co., Japan. The thicknesses of the water-wet chitosan membranes were 70 µm. The chitosan membranes were immersed in $AgNO_3$ aqueous solutions of given concentration for 48 hours in a light-shielded bottle. The resulting membranes were assembled individually in the test cell for permeation of pure propane and propylene at 23° C. These gases were humidified with water prior to entering the test cell. The pressure of the test gas was 136 psig for propylene and 109 psig for propane. The permeation fluxes of the membranes are shown in Table 1 below.

The composition of the membranes was also determined gravimetrically. Specifically, prior to immersing in an aqueous AgNO3 solution, a water-wet chitosan membrane sample was dried under vacuum at 23° C. for 8 hours and weighed. The dried chitosan sample (weight $W_0$) was immersed in the aqueous $AgNO_3$ solution for 48 hours in the light-shielded bottle. The membrane sample was taken out of the liquid solution, quickly blotted with Kimwipes the excess liquid on the membrane surface, then weighed using an analytical balance to determine its weight ($W_1$), and then placed in a dry closed container of known weight, which was connected to a vacuum system to remove water sorbed in the membrane sample. The weight of the dried membrane sample was $W_2$. Thus, the composition of the $AgNO_3$—containing chitosan membrane prepared using the given concentration of aqueous $AgNO_3$ solution was: chitosan $(W_0/W_1)\times100$ wt %, silver nitrate $(W_2-W_0)/W_1\times100$ wt %, and water $(W_1-W_2)/W_1\times100$ wt %. The composition of the membrane was also shown in Table 1 below.

TABLE 1

| Concentration of $AgNO_3$ (M) | Composition of Resulting Membrane (wt %) | | | Permeation Flux (L/m².h) | |
|---|---|---|---|---|---|
| | $AgNO_3$ | Chitosan | Water | Propylene | Propane |
| 0.2 | 12.6 | 51.4 | 36.0 | 2.7 | 0.17 |
| 0.8 | 22.4 | 47.0 | 30.6 | 9.1 | 0.03 |
| 3 | 41.3 | 32.9 | 25.8 | 14.8 | b |
| 5 | 50.8 | 29.0 | 22.2 | 16.3 | b | b: too small (<< 0.003 L/m².h) to be measured accurately.

EXAMPLE 6

Effect of Feed Gas Pressure on Permeation Flux

This example illustrates the effect of feed gas pressure on permeation flux of propylene and propane through a composite membrane. The procedure of membrane preparation was similar to that described in Example 4, except for the following:

(a) Concentration of chitosan (supplied by Koyowa Technos, Japan) in the chitosan membrane casting solution was 1.1 wt %;

(b) The substrate membrane was prepared from polysulfone (Udel 1700) by the phase inversion technique. The substrate membrane casting solution contained 12 wt % polysulfone, 11 wt % ethylene glycol monomethyl ether, and 77 wt % N,N-dimethyl acetamide. Water was used as the nonsolvent to induce polymer precipitation during the phase inversion process;

(c) The composite membrane was formed by dip coating the polysulfone substrate membrane with the chitosan solution, followed by drying in air and then alkali treatment; and (d) The composite membrane was then immersed in a light-shielded 3 M aqueous $AgNO_3$ solution for 48 hours.

Figure 3:
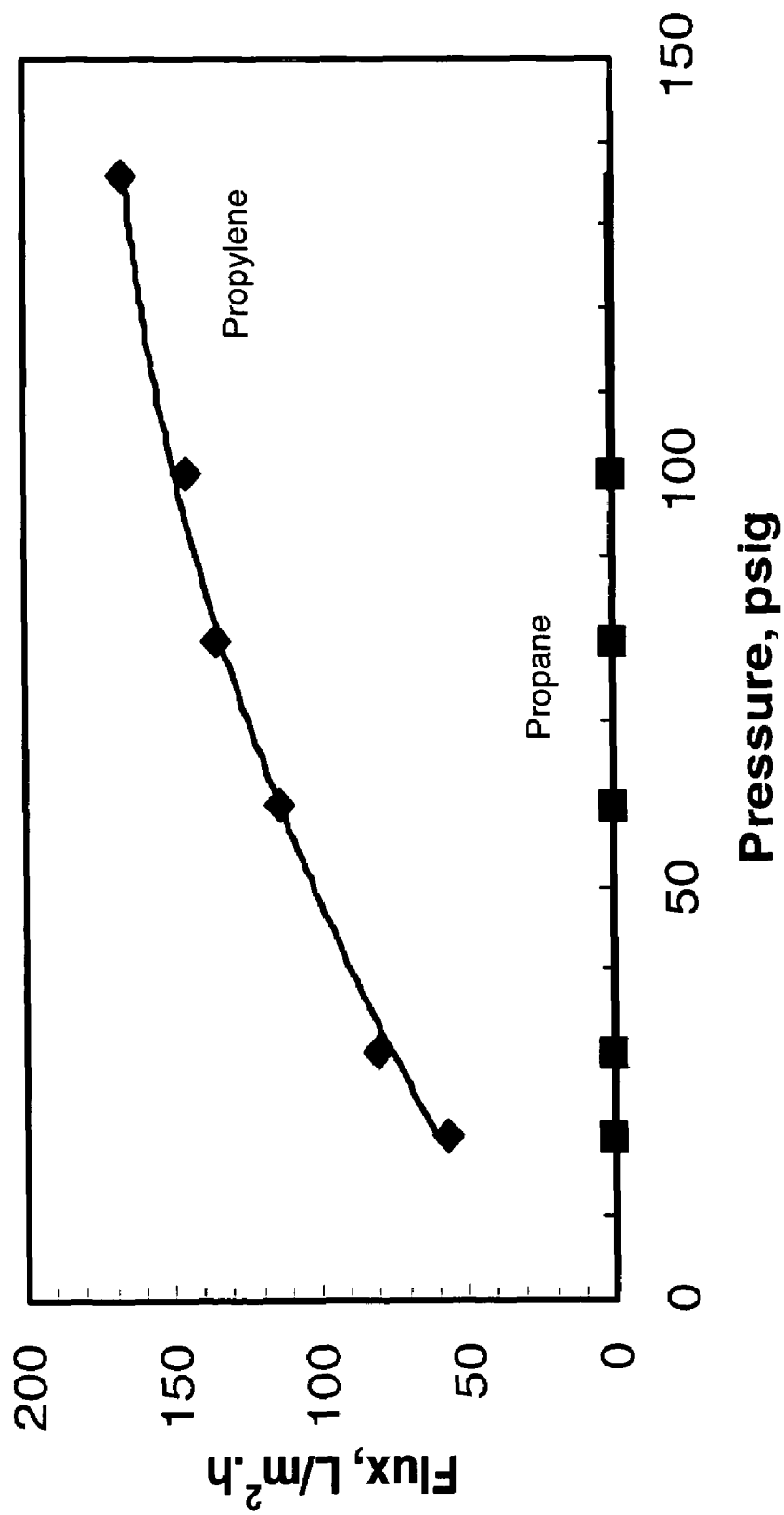
FIG. 3 is a plot of the flux rate for propylene across a chitosan membrane as determined in Example 3.

The membrane was mounted in the test cell and tested for permeation of pure propylene and propane at 23° C. The test procedure was the same as in Example 5 except that the fees gas pressure was varied, and the test results are plotted in FIG. 3

What is claimed is:

1. A process to treat a gaseous feed stream comprising from 99 to 1 mole % of one or more $C_{1-8}$ olefins and from 1 to 99 mole % of one or more $C_{1-8}$ paraffins, said stream comprising less than 500 ppm of $C_{2-4}$ acetylenes, said process comprising:
   (i) passing said stream through an adsorption bed to reduce the concentration of sulfur compounds in the stream to less than 100 ppm;
   (ii) passing the resulting stream through a humidifier so that the stream takes up at least 85% of the water required to saturate the stream;
   (iii) passing the resulting stream through a demister to remove any liquid droplets entrained in the stream;
   (iv) passing the resulting stream at a pressure from 14 to 1500 psig, and a temperature from 20° C. to 60° C. to the feed side of a composite membrane comprising a support layer permeable or semi-permeable to said olefin and a polysaccharide layer in which has been chelated from 30 to 60 weight % on a dry basis based on the weight of the polysaccharide layer of one or more compounds selected from the group consisting of copper and silver compounds capable of forming complexes with at least one olefin in said stream or a mixture thereof, so that not less than 80 mole % of the olefins in said feed stream pass through said composite membrane; and
   (v) recovering a permeate stream comprising not less than 90 mole % of olefin and not more than 10 mole % of paraffin.

2. The process according to claim 1, wherein the transmission rate of olefin across the membrane is not less than 50 sl/m²/hour.

3. The process according to claim 2, wherein in the composite membrane the polysaccharide layer has a thickness from 0.5 to 20 microns and the support layer has a thickness from 30 to 200 microns.

4. The process according to claim 3, wherein the support layer is made from one or more members selected from the group consisting of polyesters, polyamides, polyimides, polyacrylonitrile, polysulphones and polycarbonates.

5. The process according to claim 4, wherein the permeate stream comprises not less than 95 mole % of olefin and not more than 5 mole % of paraffin.

6. The process according to claim 5, wherein the feed stream comprises less than 50 ppm of acetylenes.

7. The process according to claim 6, wherein in step (i) the concentration of sulfur compounds is reduced to less than 10 ppm.

8. The process according to claim 7, wherein said silver and copper compounds are selected from the group consisting of $AgNO_3$, $AgBF_4$, and cuprous compounds.

9. The process according to claim 8, wherein the polysaccharide is chitosan.

10. The process according to claim 9, wherein the chitosan membrane has cheated therein from 45 to 55 weight % on a dry basis based on the weight of the polysaccharide layer of said cuprous compounds or silver compounds.

11. The process according to claim 10, wherein the transmission rate of olefin across the membrane is not less than 150 sl/m²/hour.

12. The process according to claim 11, wherein the olefins are $C_{2-4}$ alpha olefins.

13. The process according to claim 12, wherein in the composite membrane the support layer has a thickness from 50 to 150 microns and the chitosan layer has a thickness from 3 to 10 microns.

14. The process according to claim 13, wherein the feed stream to the membrane is at a pressure from 14 to 800 psi.

15. The process according to claim 14, wherein the compound chelated in the chitosan layer is $AgNO_3$.

16. The process according to claim 15, wherein the permeate stream comprises not less than 98 mole % of the olefins and not more than 2 mole % of the paraffin.

17. The process according to claim 16, further comprising passing the permeate stream through a dryer.

18. The process according to claim 17, further comprising recovering a retentate stream and recycling it back to a process upstream of said separation process.

19. The process according to claim 18, wherein the olefin is ethylene.

20. The process according to claim 18, wherein the olefin is propylene.

* * * * *